(12) United States Patent
Komoda

(10) Patent No.: US 9,333,182 B2
(45) Date of Patent: May 10, 2016

(54) ADHESIVE PATCH

(75) Inventor: Toshikazu Komoda, Osaka-fu (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 2 days.

(21) Appl. No.: 14/241,622

(22) PCT Filed: Aug. 31, 2012

(86) PCT No.: PCT/JP2012/072267
§ 371 (c)(1),
(2), (4) Date: Apr. 28, 2014

(87) PCT Pub. No.: WO2013/031992
PCT Pub. Date: Mar. 7, 2013

(65) Prior Publication Data
US 2014/0234393 A1  Aug. 21, 2014

(30) Foreign Application Priority Data

Aug. 31, 2011  (JP) ................................ 2011-189967

(51) Int. Cl.
*A61K 9/70* (2006.01)
*A61K 31/27* (2006.01)

(52) U.S. Cl.
CPC ............ *A61K 9/7061* (2013.01); *A61K 31/27* (2013.01)

(58) Field of Classification Search
None
See application file for complete search history.

(56) References Cited

U.S. PATENT DOCUMENTS

| | | |
|---|---|---|
| 5,602,176 A | 2/1997 | Enz |
| 6,316,023 B1 | 11/2001 | Asmussen et al. |
| 6,689,379 B1 | 2/2004 | Bracht |
| 2007/0128263 A1 | 6/2007 | Gargiulo et al. |
| 2010/0087768 A1 | 4/2010 | Forlano et al. |
| 2013/0261571 A1 | 10/2013 | Prinz et al. |

FOREIGN PATENT DOCUMENTS

| | | | |
|---|---|---|---|
| EP | 1437130 | * 10/2002 | ............ A61K 9/70 |
| EP | 1 437 130 | 7/2004 | |
| EP | 1 696 013 | 8/2006 | |
| JP | 06-065066 | 3/1994 | |
| JP | 2002-542277 | 12/2002 | |
| JP | 2005-008627 | 1/2005 | |
| JP | 2007-326844 | 12/2007 | |
| JP | 2011-6352 | 1/2011 | |
| JP | 2011-006352 | * 1/2011 | ............ A61K 47/32 |
| WO | 2006/121560 | 11/2006 | |
| WO | 2009/113504 | 9/2009 | |
| WO | 2011/076621 | 6/2011 | |
| WO | 2011/118683 | 9/2011 | |
| WO | WO 2011/118683 | * 9/2011 | ............ A61K 31/27 |
| WO | WO 2012/012417 | * 1/2012 | ............ C09J 4/06 |

OTHER PUBLICATIONS

Extended European Search Report issued Jan. 12, 2015 in European Application No. 12826910.7.
International Search Report issued Nov. 6, 2012 in International (PCT) Application No. PCT/JP2012/072267.

* cited by examiner

*Primary Examiner* — Brian Gulledge
(74) *Attorney, Agent, or Firm* — Wenderoth, Lind & Ponack, L.L.P.

(57) ABSTRACT

Provided is an adhesive patch which has excellent rivastigmine storage stability and an increased skin permeability of rivastigmine to such an extent that the amount of percutaneous absorption required for treating Alzheimer's disease is obtained.

This adhesive patch includes a backing and an adhesive layer containing rivastigmine and an alkyl (meth)acrylate-based copolymer that does not contain any acrylic monomer component having a carboxy group, the adhesive layer being laid on one side of and integrated with the backing.

6 Claims, No Drawings

ADHESIVE PATCH

FIELD

The present invention relates to an adhesive patch which has excellent rivastigmine storage stability and an increased skin permeability of rivastigmine to such an extent that the amount of percutaneous absorption required for treating Alzheimer's disease is obtained.

BACKGROUND

Recently, dementia patients associated with Alzheimer's disease have been increasing with the growing number of the elderly population. Anticholinesterase agents such as donepezil hydrochloride and rivastigmine tartrate have been developed as anti-dementia drugs for Alzheimer's disease. These agents have been prescribed for dementia patients as oral preparations such as tablets and liquids in clinical practice.

However, dementia patients often have difficulty in taking therapeutic agents by themselves because advanced dementia causes poor medication compliance or decreased swallowing function. Accordingly, development of transdermal agents has been needed which can solve these problems to achieve stable administration of therapeutic agents.

Now, transdermal agents are being developed using rivastigmine as one of anti-dementia drugs for Alzheimer's disease. However, lotions prepared using rivastigmine increased the skin permeability of the drug just after administration but had difficulty in keeping continuous cutaneous absorption of the drug in an amount sufficient to obtain a desired drug effect for one day or longer. In addition, adhesive patches prepared using rivastigmine had difficulty in stably containing a high concentration of rivastigmine, which is liquid at room temperature, in a medicated layer. For this reason, it is difficult for adhesive patches to increase the skin permeation of rivastigmine to such an extent that a desired drug effect is obtained. In order to solve these problems, various studies have been made on adhesive patches containing rivastigmine.

Patent Literature 1 describes an adhesive patch which includes in combination rivastigmine tartrate, an acrylic adhesive (such as alkyl amino methacrylate copolymer), an acrylic acid polymer, and a surfactant. However, there is no description of the storage stability of rivastigmine tartrate in the adhesive patch and the skin permeability of rivastigmine in Patent Literature 1.

Patent Literature 2 describes an adhesive patch which includes in combination rivastigmine, polymethacrylate, an acrylate copolymer containing a carboxy group, and an antioxidant. Patent Literature 2 describes that the antioxidant was used for suppressing decomposition of rivastigmine in the adhesive patch and the antioxidant improved the storage stability of rivastigmine. However, there is no description of the skin permeability of rivastigmine in the adhesive patch in Patent Literature 2.

Patent Literature 3 describes an adhesive patch with a two-layer structure composed of, in combination, a storage layer comprising rivastigmine, a polyacrylate adhesive containing a carboxy group, an acrylate copolymer, and vitamin E; and a silicone adhesive layer comprising a silicone adhesive, a silicone oil, and vitamin E. Patent Literature 3 describes that such an adhesive patch has excellent adhesion to the skin and skin permeability. However, the storage layer and the adhesive layer are laid on each other after these two layers are separately produced, requiring a complex process for producing the adhesive patch in Patent Literature 3. In addition, rivastigmine, vitamin E used as an antioxidant, and other components move between the storage layer and the adhesive layer during the storage of the adhesive patch, so that the skin permeability of rivastigmine in the adhesive patch may change depending on the storage period of the adhesive patch.

Patent Literature 4 discloses an adhesive patch which includes in combination rivastigmine, an acrylic adhesive without containing any cross-linking agent containing a metal atom, and a volatilization inhibitor such as squalane and triethyl citrate. Pressure-sensitive acrylic polymers having a carboxy group in a side chain were disclosed as examples of suitable acrylic adhesives in the patent literature 4. The volatilization inhibitor is used for suppressing loss of rivastigmine due to volatilization of rivastigmine during the production, which rivastigmine is liquid at room temperature. Patent Literature 4 discloses the study on improvement in the adhesion of the adhesive patch but has no description on the storage stability of rivastigmine.

CITATION LIST

Patent Literature

Patent Literature 1: U.S. Pat. No. 5,602,176B
Patent Literature 2: U.S. Pat. No. 6,316,023B
Patent Literature 3: U.S. Patent Application Laid-Open Publication No. 2007/128263A
Patent Literature 4: U.S. Patent Application Laid-Open Publication No. 2010/087768A

SUMMARY

Technical Problem

It is an object of the present invention to provide an adhesive patch which has excellent rivastigmine storage stability and which has an increased skin permeability of rivastigmine to such an extent that the amount of percutaneous absorption required for treating Alzheimer's disease is obtained.

Solution to Problems

The present inventor has intensively studied in light of the above-mentioned problems and has found that an alkyl (meth)acrylate-based copolymer without containing any acrylic monomer component having a carboxy group provides excellent rivastigmine storage stability and can significantly decrease decomposition and volatilization of rivastigmine without containing an antioxidant which was contained in the case of Patent Literatures 2 and 3 or without using a volatilization inhibitor for rivastigmine which was used in the case of Patent Literature 4.

Alkyl (meth)acrylate-based copolymers containing an acrylic monomer component having a carboxy group have been used in Examples in all of Patent Literatures 1 to 4, and, in particular, have been described as a suitable acrylic adhesive in Patent Literature 4. In the adhesive patches of Patent Literatures 1 to 4, the alkyl (meth)acrylate-based copolymers have been used as bases of medicated layers and used with additives such as an antioxidant and a volatilization inhibitor to improve the rivastigmine adhesive patches. On the other hand, the alkyl (meth)acrylate-based copolymer without containing any acrylic monomer component having a carboxy group itself unexpectedly provides excellent rivastigmine storage stability without using any additive such as an antioxidant and a volatilization inhibitor.

The present invention has been completed on the basis of the above-mentioned finding. The adhesive patch of the present invention is characterized as follows.

[1] An adhesive patch including: a backing; and an adhesive layer containing rivastigmine and an alkyl (meth)acrylate-based copolymer without containing any acrylic monomer component having a carboxy group, the adhesive layer being laid on one side of and integrated with the backing.

[2] The adhesive patch according to aspect [1], wherein the alkyl (meth)acrylate-based copolymer includes an alkyl (meth)acrylate component having an alkyl group with 1 to 16 carbon atoms.

[3] The adhesive patch according to aspect [1], wherein the alkyl (meth)acrylate-based copolymer includes a 1-vinyl-2-pyrrolidone component.

[4] The adhesive patch according to aspect [1], wherein the alkyl (meth)acrylate-based copolymer includes a copolymer (A) containing a 2-ethylhexyl (meth)acrylate component and an alkyl (meth)acrylate component having an alkyl group with six or more carbon atoms except 2-ethylhexyl (meth)acrylate.

[5] The adhesive patch according to aspect [1], wherein the alkyl (meth)acrylate-based copolymer includes a copolymer (B) containing a 1-vinyl-2-pyrrolidone component and an alkyl acrylate component having an alkyl group with 1 to 12 carbon atoms.

[6] The adhesive patch according to aspect [1], wherein rivastigmine is in a free base form.

[7] The adhesive patch according to aspect [1], wherein the adhesive layer does not contain an antioxidant and a rivastigmine volatilization inhibitor.

Advantageous Effects of Invention

In the adhesive patch of the present invention, the alkyl (meth)acrylate-based copolymer having the above composition is used to provide excellent rivastigmine storage stability and an increased skin permeability of rivastigmine to such an extent that the amount of percutaneous absorption required for treating Alzheimer's disease is obtained.

In the phrase "an increased skin permeability of rivastigmine to such an extent that the amount of percutaneous absorption required for treating Alzheimer's disease is obtained" used herein, the skin permeability is determined to be "increased" when the cumulative absorbed amount is 0.3 mg/cm$^2$/24 hr or more, which is obtained in the skin permeability test.

DESCRIPTION OF EMBODIMENTS

The adhesive patch of the present invention has a backing and an adhesive layer laid on one side of and integrated with the backing.

The adhesive layer contains rivastigmine. Rivastigmine, [(S)—N-ethyl-N-methyl-3-[1-(dimethylamino)ethyl]-phenyl carbamate], is a liquid compound at room temperature and used as a therapeutic agent for Alzheimer's disease due to its acetylcholinesterase inhibitory action.

Rivastigmine either in a free base form or in an acid addition salt form can be used in the adhesive patch of the present invention. Rivastigmine in a free base form is particularly suitable. The term "rivastigmine" used herein means both the free base form and the acid addition salt form unless otherwise specified.

A low rivastigmine content in the adhesive layer not only produces difficulty in attaining the percutaneous absorption rate of rivastigmine required for obtaining a desired drug effect, but also increases the amount of rivastigmine volatilizing from the adhesive layer to an unignorable level relative to the content of rivastigmine in the adhesive layer during the storage of the adhesive patch, thereby decreasing the storage stability. On the other hand, a high rivastigmine content in the adhesive layer leads to overplasticization of an adhesive because of the plasticizing action of rivastigmine and thus decreases the cohesion of the adhesive layer, which may cause the adhesive layer to extend from the adhesive patch over time during the storage of the adhesive patch or may cause the adhesive layer to remain on the skin when removing the adhesive patch from the skin. Accordingly, the content of rivastigmine in the adhesive layer is preferably 2 to 50% by weight, more preferably 3 to 45% by weight, still more preferably 5 to 40% by weight, particularly preferably 7 to 36% by weight, particularly more preferably 10 to 36% by weight, and most preferably 12 to 30% by weight.

The adhesive layer contains an alkyl (meth)acrylate-based copolymer. The alkyl (meth)acrylate-based copolymer does not contain any acrylic monomer component having a carboxy group as a copolymer component. (Meth)acrylic acid used herein means acrylic acid or methacrylic acid.

The alkyl (meth)acrylate-based copolymer contains an alkyl (meth)acrylate component. The content of the alkyl (meth)acrylate component in the alkyl (meth)acrylate-based copolymer is preferably 40% by weight or more.

The number of carbon atoms in the alkyl group of the alkyl (meth)acrylate is preferably 1 to 16, more preferably 1 to 14, particularly preferably 2 to 14, and most preferably 2 to 12.

Preferred examples of the alkyl (meth)acrylates include esters of (meth)acrylic acid and a monohydric aliphatic alcohol represented by R—OH (wherein R represents a linear, branched, or cyclic alkyl group). The number of carbon atoms in the alkyl group R is preferably 1 to 16, more preferably 1 to 14, particularly preferably 2 to 14, and most preferably 2 to 12.

One or more hydrogen atoms of the alkyl group in the alkyl (meth)acrylate may be substituted by a hydroxy group(s).

Examples of the alkyl (meth)acrylate include methyl (meth)acrylate, ethyl (meth)acrylate, n-propyl (meth)acrylate, isopropyl (meth)acrylate, n-butyl (meth)acrylate, isobutyl (meth)acrylate, hexyl (meth)acrylate, n-octyl (meth)acrylate, isooctyl (meth)acrylate, 2-ethylhexyl (meth)acrylate, decyl (meth)acrylate, dodecyl (meth)acrylate, tridecyl (meth)acrylate, hexadecyl (meth)acrylate, cyclododecyl (meth)acrylate, cyclohexyl (meth)acrylate, hydroxyethyl acrylate, and hydroxypropyl acrylate. These may be used singly or may be used in combination of two or more. As used herein, (meth)acrylate means methacrylate or acrylate.

Of these, ethyl (meth)acrylate, n-octyl (meth)acrylate, 2-ethylhexyl (meth)acrylate, and dodecyl (meth)acrylate are preferred as the alkyl (meth)acrylate.

The alkyl (meth)acrylate-based copolymer preferably includes an n-octyl (meth)acrylate component or a 2-ethylhexyl (meth)acrylate component. The content of the n-octyl (meth)acrylate component or the 2-ethylhexyl (meth)acrylate component in the alkyl (meth)acrylate-based copolymer is preferably 40% by weight or more.

The alkyl (meth)acrylate-based copolymer may include other monomer components than the alkyl (meth)acrylate component.

Examples of other monomers include 1-vinyl-2-pyrrolidone, acrylamide, dimethylacrylamide, acrylonitrile, dimethylaminoethyl (meth)acrylate, t-butylaminoethyl (meth)

acrylate, vinyl acetate, and vinyl propionate. These may be used singly or may be used in combination of two or more. Of these, 1-vinyl-2-pyrrolidone is preferred.

In the present invention, the alkyl (meth)acrylate-based copolymer used in the adhesive layer does not contain any component derived from acrylic monomers having a carboxy group, as mentioned above. Specific examples of the acrylic monomers having a carboxy group include (meth)acrylic acid and alkyl (meth)acrylates in which one or more hydrogen atoms in the alkyl group are substituted by a carboxy group(s) (also referred to as "carboxyalkyl (meth)acrylates"). Examples of the carboxyalkyl (meth)acrylates include 2-carboxyethyl (meth)acrylate, 2-carboxypropyl (meth)acrylate, 3-carboxypropyl (meth)acrylate, and 4-carboxybutyl (meth)acrylate. Commercial products of the alkyl (meth)acrylate-based copolymer containing a component derived from carboxyalkyl (meth)acrylates include Durotak 387-2353, 387-2051, and 387-2052 produced by National Starch & Chemical Co.

When the alkyl (meth)acrylate-based copolymer is produced by the polymerization using the acrylic monomer having a carboxy group, the carboxy group is not involved in a polymerization reaction. Accordingly, the alkyl (meth)acrylate-based copolymer produced by the polymerization using the acrylic monomer having a carboxy group also has a carboxy group. The carboxy group of the alkyl (meth)acrylate-based copolymer is present in the adhesive layer as a carboxy group (—COOH) or as a free carboxy group (—COO⁻) from which the proton is released. Such a carboxy group and a free carboxy group are supposed to promote decomposition of rivastigmine and thus decrease the storage stability of rivastigmine.

Therefore, in the present invention, the alkyl (meth)acrylate-based copolymer contained in the adhesive layer does not contain any component derived from acrylic monomers having a carboxy group. However, in order to further reduce decomposition of rivastigmine, the alkyl (meth)acrylate-based copolymer contained in the adhesive layer preferably does not contain a carboxy group. Accordingly, monomers to be polymerized for producing the alkyl (meth)acrylate-based copolymer also preferably do not contain a carboxy group.

In the adhesive layer, the alkyl (meth)acrylate-based copolymer preferably has no cross-linking by a cross-linking agent. Examples of the cross-linking agent include epoxy compounds, polyisocyanate compounds, metal chelate compounds, and metal alkoxide compounds. The crosslinking agent is used to crosslink the alkyl (meth)acrylate-based copolymer when producing the adhesive layer, thereby suppressing leak or cold flow of rivastigmine from the adhesive layer. However, the cross-linking agent promotes decomposition of rivastigmine to decrease the storage stability.

The adhesiveness of the adhesive patch and the releasability of rivastigmine can be adjusted by controlling the types and the copolymerization ratio of the monomer components such as the alkyl (meth)acrylate and 1-vinyl-2-pyrrolidone in the alkyl (meth)acrylate-based copolymer.

Preferred examples of the alkyl (meth)acrylate-based copolymers include a copolymer (A) containing a 2-ethylhexyl (meth)acrylate component and an alkyl (meth)acrylate component having an alkyl group with six or more carbon atoms except 2-ethylhexyl (meth)acrylate.

The number of carbon atoms of the alkyl group in the alkyl (meth)acrylate except 2-ethylhexyl (meth)acrylate is preferably six or more and more preferably 6 to 16.

Examples of the alkyl (meth)acrylates having an alkyl group with six or more carbon atoms except 2-ethylhexyl (meth)acrylate include hexyl (meth)acrylate, n-octyl (meth)acrylate, isooctyl (meth)acrylate, decyl (meth)acrylate, dodecyl (meth)acrylate, tridecyl (meth)acrylate, hexadecyl (meth)acrylate, cyclododecyl (meth)acrylate, cyclohexyl (meth)acrylate, hydroxyethyl acrylate, and hydroxypropyl acrylate. These may be used singly or may be used in combination of two or more. Of these, dodecyl (meth)acrylate is preferred.

The copolymer (A) preferably contains a 2-ethylhexyl acrylate component, a 2-ethylhexyl methacrylate component, and a dodecyl (meth)acrylate component.

The content of the 2-ethylhexyl (meth)acrylate component in the copolymer (A) is preferably 40 to 95% by weight, more preferably 70 to 95% by weight, and particularly preferably 75 to 95% by weight.

The content of the alkyl (meth)acrylate component having an alkyl group with six or more carbon atoms except 2-ethylhexyl (meth)acrylate in the copolymer (A) is preferably 5 to 60% by weight, more preferably 5 to 30% by weight, and particularly preferably 10 to 25% by weight.

Preferred examples of the alkyl (meth)acrylate-based copolymers include a copolymer (B) containing a 1-vinyl-2-pyrrolidone component and an alkyl acrylate component having an alkyl group with 1 to 12 carbon atoms.

Examples of the alkyl acrylates having an alkyl group with 1 to 12 carbon atoms include methyl acrylate, ethyl acrylate, n-propyl acrylate, isopropyl acrylate, n-butyl acrylate, isobutyl acrylate, hexyl acrylate, n-octyl acrylate, isooctyl acrylate, 2-ethylhexyl acrylate, decyl acrylate, and dodecyl acrylate. These may be used singly or may be used in combination of two or more. Of these, ethyl acrylate and n-octyl acrylate are preferred.

The content of the alkyl acrylate component having an alkyl group with 1 to 12 carbon atoms in the copolymer (B) is preferably 40 to 95% by weight, more preferably 70 to 95% by weight, and particularly preferably 80 to 95% by weight.

The content of the 1-vinyl-2-pyrrolidone component in the copolymer (B) is preferably 5 to 60% by weight, more preferably 5 to 30% by weight, and particularly preferably 5 to 20% by weight.

The alkyl (meth)acrylate-based copolymer may be produced by conventionally well-known polymerization methods. Examples of the polymerization methods for producing the alkyl (meth)acrylate-based copolymer include solution polymerization of the above monomers in the presence of a polymerization initiator. A polymerization method preferably used for producing the alkyl (meth)acrylate-based copolymer involves supplying predetermined amounts of monomers, a polymerization initiator, and a solvent to a reactor equipped with a stirrer and a cooling reflux device for an evaporated solvent; and heating them at a temperature of from 60 to 80° C. for 4 to 48 hours to undergo a radical polymerization reaction of the monomers.

Examples of the polymerization initiator include azobis polymerization initiators such as 2,2'-azobisisobutyronitrile (AIBN), 1,1'-azobis(cyclohexane-1-carbonitrile), and 2,2'-azobis(2,4'-dimethylvaleronitrile); and organic peroxides such as benzoyl peroxide (BPO), lauroyl peroxide (LPO), and di-tert-butyl peroxide. Examples of the solvent include ethyl acetate and toluene. Furthermore, the polymerization reaction is preferably carried out under a nitrogen gas atmosphere.

When the adhesive layer has a low content of the alkyl (meth)acrylate-based copolymer, the cohesion of the adhesive layer may be insufficient. The adhesive layer with insufficient cohesion may cause a problem in that the adhesive layer remains on the skin when the adhesive patch is removed from the skin. When the adhesive layer has a high content of the alkyl (meth)acrylate-based copolymer, a predetermined amount of rivastigmine may not be contained in the adhesive layer so that a sufficient amount of rivastigmine can be released from the adhesive layer. Therefore, the content of the alkyl (meth)acrylate-based copolymer in the adhesive layer is preferably 50 to 95% by weight, more preferably 60 to 90% by weight, particularly preferably 64 to 85% by weight, and most preferably 70 to 85% by weight.

The adhesive layer formed using the alkyl (meth)acrylate-based copolymer mentioned above provides good storage stability of the adhesive patch even if containing a large amount of rivastigmine; has proper adhesive strength but never remains on the skin when removed from the skin; and can further increase the transdermal absorbability of rivastigmine. Therefore, the alkyl (meth)acrylate-based copolymer is suitably used as an adhesive for carrying rivastigmine.

Conventional adhesive patches had problems in that rivastigmine decomposed during the storage of the adhesive patches to decrease the storage stability and rivastigmine evaporated during the production of the adhesive patches to decrease the content of rivastigmine unless the adhesive patches contained an antioxidant or a volatilization inhibitor for rivastigmine. However, the adhesive patch of the present invention avoids addition of an antioxidant or a volatilization inhibitor because the alkyl (meth)acrylate-based copolymer provides excellent rivastigmine storage stability.

The adhesive layer preferably contains other additives such as a compatibilizer and a filler as long as they do not impair the physical properties of the adhesive layer.

The compatibilizer can improve the compatibility between rivastigmine and the alkyl (meth)acrylate-based copolymer to increase the storage stability of rivastigmine. Such a compatibilizer is not particularly limited as long as it is an additive compatible with both rivastigmine and acrylic adhesives. Examples of the compatibilizer include esters such as isopropyl myristate, decyl oleate, and isopropyl adipate; monohydric alcohols such as myristyl alcohol, cetanol, octyldodecanol, isostearyl alcohol, and stearyl alcohol; dihydric alcohols such as octanediol; acids such as oleic acid and stearic acid; and liquid paraffin. Of these, monohydric alcohols such as myristyl alcohol, cetanol, octyldodecanol, isostearyl alcohol, and stearyl alcohol are preferred, and stearyl alcohol is more preferred.

A high content of the compatibilizer in the adhesive layer may decrease the cohesion of the adhesive layer and cause the adhesive layer to remain on the skin when the adhesive patch is removed from the skin. Therefore, the content of the compatibilizer in the adhesive layer is preferably 20% by weight or less, more preferably 0.01 to 10% by weight, and particularly preferably 0.1 to 5% by weight.

The filler can control the adhesive strength of the adhesive layer. Examples of the filler include inorganic fillers such as silicic anhydride, titanium oxide, and zinc oxide; organic metal salts such as calcium carbonate and magnesium stearate; cellulose derivatives such as lactose, crystalline cellulose, ethyl cellulose, and low-substituted hydroxypropyl cellulose; polyacrylic acid, and polymethacrylic acid. Of these, inorganic fillers such as silicic anhydride, titanium oxide, and zinc oxide are preferred, and silicic anhydride is more preferred.

A high content of the filler in the adhesive patch may decrease the adhesive strength of the adhesive patch excessively. Therefore, the filler in the adhesive layer is preferably 5% by weight or less, more preferably 0.01 to 5% by weight, and particularly preferably 0.1 to 1% by weight.

Although two or more adhesive layers may be laid on one side of and integrated with the backing, it is preferred that only a single adhesive layer be laid on one side of and integrated with the backing.

A thin adhesive layer may fail to contain a sufficient amount of rivastigmine required for obtaining a desired drug blood level. A thick adhesive layer may cause the adhesive layer to extend from the backing or may decrease the adherence of the adhesive patch during the storage or use of the adhesive patch, or may require time for removing a solvent during the production of the adhesive layer to decrease production efficiency of the adhesive patch. Therefore, the thickness of the adhesive layer is preferably 10 to 500 µm, more preferably 50 to 250 µm, particularly preferably 50 to 200 µm, and most preferably 70 to 150 µm.

The backing on which the adhesive layer is integrally superposed is used for preventing loss of the drug in the adhesive layer to protect the adhesive layer. In addition, the backing is required to have the strength for imparting a self-supporting characteristic to the adhesive patch while having the flexibility for imparting good adherence to the adhesive patch.

Such a backing is not particularly limited and examples thereof include non-foamed resin films, foamed resin films, nonwoven fabrics, woven fabrics, knitted fabrics, aluminum films, and laminated films in combination of these.

Examples of resins that constitute non-foamed resin films and foamed resin films include cellulose acetate, ethyl cellulose, rayon, polyethylene terephthalate, a plasticized vinyl acetate-vinyl chloride copolymer, nylon, an ethylene-vinyl acetate copolymer, plasticized polyvinyl chloride, polyurethane, polyethylene, polypropylene, and polyvinylidene chloride. Polyethylene terephthalate is preferred.

Examples of materials that constitute nonwoven fabrics include polyethylene, polypropylene, an ethylene-vinylacetate copolymer, an ethylene-methyl (meth)acrylate copolymer, nylon, polyester, vinylon, an SIS copolymer, an SEBS copolymer, rayon, and cotton. Polyester is preferred.

As the backing, a laminated film formed by integrally laminating a nonwoven fabric and a non-foamed resin, and a polyethylene terephthalate film are preferred, and a polyethylene terephthalate film is more preferred, from the viewpoint of the flexibility and the effect of preventing loss of rivastigmine.

In order to prevent loss of the drug in the adhesive layer and protect the adhesive layer, the adhesive layer is preferably coated with and protected by a removable release liner.

Examples of the release liners include release bases in which a release treatment is conducted on the side facing the adhesive layer. Examples of the release bases include resin films made of polyethylene terephthalate, polyethylene, polypropylene, polyvinyl chloride, polyvinylidene chloride, or the like, and papers. The release treatment is conducted by, for example, applying a release agent such as silicone to the side of the release base facing the adhesive layer.

In order to improve the barrier property of the release liner, it is preferred that an aluminum foil or an aluminum deposited layer be laid on and integrated with the release liner. Furthermore, when the release base is made of paper, the release base made of paper may be impregnated with a resin such as polyvinyl alcohol in order to improve the barrier property of the release base.

Next, methods for producing the adhesive patch of the present invention will be described. Although methods for producing the adhesive patch are not particularly limited, examples thereof include: a method (1) including adding rivastigmine, the alkyl (meth)acrylate-based copolymer, and optional additives to a solvent such as ethyl acetate, stirring until the mixture becomes uniform to obtain an adhesive layer solution, then applying the adhesive layer solution to one side of a backing, followed by drying to obtain an adhesive layer laid on one side of and integrated with the backing, and optionally superposing a release liner on the adhesive layer so that the side of the release liner on which the release treatment is conducted faces the adhesive layer; and a method (2) including adding rivastigmine, the alkyl (meth)acrylate-based copolymer, and optional additives to a solvent such as ethyl acetate, stirring until the mixture becomes uniform to obtain an adhesive layer solution, then applying the adhesive layer solution to the side of a release liner on which the release treatment is conducted, followed by drying to form an adhesive layer on the release liner, and superposing a backing on and integrating it with the adhesive layer.

EXAMPLE

Although the present invention will be described below in more detail by way of Examples, the present invention is not limited thereto.

(Preparation of Acrylic Adhesive A)

An acrylic adhesive A was prepared in the following manner. A reaction liquid containing monomers including 13 parts by weight of dodecyl methacrylate, 78 parts by weight of 2-ethylhexyl methacrylate, and 9 parts by weight of 2-ethylhexyl acrylate, and 50 parts by weight of ethyl acetate was supplied to a 40-L polymerization apparatus. Subsequently, a nitrogen atmosphere at 80° C. was maintained in the polymerization apparatus. To the reaction liquid, a polymerization initiator solution prepared by dissolving 0.5 parts by weight of benzoyl peroxide in 50 parts by weight of cyclohexane was added over 24 hours to copolymerize the above monomers. After the completion of the polymerization, ethyl acetate was further added to the reaction liquid to obtain an acrylic adhesive solution A containing 35% by weight of the acrylic adhesive A including a dodecyl methacrylate/2-ethylhexyl methacrylate/2-ethylhexyl acrylate copolymer.

(Preparation of Acrylic Adhesive B)

An acrylic adhesive B was prepared in the following manner. A reaction liquid containing monomers including 100 parts by weight of ethyl acrylate, 80 parts by weight of n-octyl acrylate, and 20 parts by weight of 1-vinyl-2-pyrrolidone, and 200 parts by weight of ethyl acetate was supplied to a separable flask. Subsequently, a nitrogen atmosphere at 80° C. was maintained in the separable flask. To the reaction liquid, a polymerization initiator solution prepared by dissolving 1 part by weight of benzoyl peroxide in 100 parts by weight of ethyl acetate was added over 27 hours to polymerize the above monomers. After the completion of the polymerization, ethyl acetate was further added to the reaction liquid to obtain an acrylic adhesive solution B containing 32% by weight of the acrylic adhesive B including an ethyl acrylate/n-octyl acrylate/1-vinyl-2-pyrrolidone copolymer.

(Preparation of Acrylic Adhesive C)

An acrylic adhesive C was prepared in the following manner. A reaction liquid containing monomers including 190 parts by weight of 2-ethylhexyl acrylate and 10 parts by weight of acrylic acid, and 50 parts by weight of ethyl acetate was supplied a 40-L polymerization apparatus. Subsequently, a nitrogen atmosphere at 80° C. was maintained in the polymerization apparatus. To the reaction liquid, a polymerization initiator solution prepared by dissolving 0.5 parts by weight of benzoyl peroxide in 50 parts by weight of cyclohexane was added over 24 hours to copolymerize the monomers. After the completion of the polymerization, ethyl acetate was further added to the reaction liquid to obtain an acrylic adhesive solution C containing 35% by weight of the acrylic adhesive C including a 2-ethylhexyl acrylate/acrylic acid copolymer.

Examples 1 to 12

Rivastigmine, the acrylic adhesive solution A, the acrylic adhesive solution B, stearyl alcohol (produced by Kokyu Alcohol Kogyo Co. Ltd.), and light silicic anhydride (A200, produced by Nippon Aerosil Co., Ltd.) were mixed. Ethyl acetate was added thereto as a solvent so that the concentration of the solid content was 25% by weight, and then mixed until the mixture becomes uniform to produce an adhesive layer solution.

Next, silicone was applied to one side of a release base composed of a 38-µm-thick polyethylene terephthalate film to prepare a release liner on which the release treatment was conducted. The adhesive layer solution was applied to the release-treated side of the release liner, followed by drying at 80° C. for 30 minutes to produce a laminate in which an adhesive layer with the thickness shown in Table 1 was formed on the release-treated side of the release liner. The content of each component in the adhesive layer was shown in Table 1.

A backing composed of a 38-µm-thick polyethylene terephthalate film was then provided. The backing and the laminate were laid on each other so that one side of the backing faced the adhesive layer of the laminate, and the adhesive layer of the laminate was transferred to the backing to achieve integral lamination, thereby producing an adhesive patch.

Comparative Examples 1 to 4

An adhesive layer solution was produced in the same manner as in Example 1 except that rivastigmine, the acrylic adhesive solution C, polyisocyanate, high molecular weight polyisobutylene (Oppanol B-100, produced by BASF), medium molecular weight polyisobutylene (Himol 5H, produced by JX Nippon Oil & Energy Corporation), a styrene-isoprene-styrene block copolymer (produced by JSR Corporation), a hydrogenated petroleum resin (ARKON P-85, produced by Arakawa Chemical Industries, Ltd.), a silicone adhesive (Bio PSA Q7-4302, produced by The Dow Chemical Company), and a silicone oil (Q7-9120, produced by The Dow Chemical Company) were mixed so as to obtain an adhesive layer having the content of each component as shown in Table 2. An adhesive patch was obtained using this adhesive layer solution. In Comparative Examples 2 to 4, toluene was used as a solvent instead of ethyl acetate during the production of the adhesive layer solution.

The storage stability (drug concentration) and the storage stability (anti-cold flow property) of the adhesive patches obtained in Examples and Comparative Examples were measured in the following manner. In addition, the permeability test and the patch test were conducted for the adhesive patches obtained in Examples and Comparative Examples in the following manner. These results were shown in Tables 1 and 2.

[Storage Stability: Drug Concentration]

Six specimens with an area of 3 cm$^2$ were cut out of the adhesive patch just produced, and enclosed in a light-shielding packaging material. Subsequently, three specimens were stored at 4° C. and the other three specimens were stored at 60° C. for two weeks. After the storage, the weight Wt (g) of each specimen was measured. After the release liner was removed, rivastigmine in the adhesive layer was extracted using an extraction liquid (ethyl acetate:methanol (by weight ratio)=3:2) and the weight Wr (g) of rivastigmine in the adhesive layer was quantified using HPLC. The backing was washed with ethyl acetate or toluene followed by drying, and the weight Wp (g) thereof together with the weight of the release liner and the backing was measured. The rivastigmine concentration in the adhesive layer was calculated using the following Formula (1).

Rivastigmine concentration (%)=[$Wr/(Wt-Wp)$]×100    Formula (1)

The mean of the rivastigmine concentration in the adhesive layer of three specimens stored at 4° C. was defined as $C_4$ and the mean of the rivastigmine concentration in the adhesive layer of three specimens stored at 60° C. was defined as $C_{60}$ to calculate the residual ratio of rivastigmine using the following Formula (2).

Rivastigmine Residual Ratio (%)=$C_{60}/C_4$×100    Formula (2)

[Storage Stability (Anti-Cold Flow Property)]

Six specimens with an area of 3 cm$^2$ were cut out of the adhesive patch just produced, and each specimen was measured for its weight and enclosed in a light-shielding packaging material. Three specimens were stored at 4° C. and the other three specimens were stored at 60° C. for two weeks. After the storage, the specimens were taken out of the packaging material. If the adhesive layer extended from the periphery of the specimen, the extending part was removed from the specimen and the weight of the specimen was measured. The total weight of the specimens stored at 4° C. was defined as $T_4$ and the total weight of three specimens stored at 60° C. was defined as $T_{60}$ to calculate the ratio of weight change of the adhesive layer using the following Formula (3).

Ratio (%) of Weight Change of Adhesive Layer=$T_{60}/T_4$×100    Formula (3)

[Permeability Test]

A specimen with a diameter of 2 cm was cut out of the adhesive patch just produced. On the other hand, a skin excised from the back of a hairless mouse (male, 8 to 10 week old) was fixed to a Franz-type diffusion cell maintained at 37° C. The specimen was pasted on the upper side of this skin with the adhesive layer of the specimen. The lower side of the skin was immersed in a receptor solution. A physiological saline adjusted at pH 7.2 was used as the receptor solution.

At 24 hours after pasting the specimen on the skin, the receptor solution under the skin was collected to measure the rivastigmine concentration using HPLC. In addition, three specimens were prepared and the rivastigmine concentration at 24 hours was measured for each specimen in the above manner. Then, the amount of rivastigmine permeation was calculated from the rivastigmine concentration and the volume of the receptor solution. The arithmetic mean of the amount of rivastigmine permeation calculated for each specimen was obtained and taken as the cumulative amount of skin permeation of rivastigmine (mg/cm$^2$/24 hr).

[Patch Test]

A specimen with an area of 5 cm$^2$ was cut out of the adhesive patch just produced and the specimen was pasted on the skin of the shaved back of a rabbit (male, 16 to 18 week old). The pasting conditions of the specimen at 6 hours and 24 hours after pasting were observed. In Table 1, the case where no change was observed when compared with the state just after pasting was evaluated as "good," the case where the adhesive patch fell off the skin was evaluated as "very bad," and the case where the adhesive patch did not fall off but the pasting position was shifted was evaluated as "bad."

TABLE 1

| | | EXAMPLE 1 | EXAMPLE 2 | EXAMPLE 3 | EXAMPLE 4 | EXAMPLE 5 | EXAMPLE 6 |
|---|---|---|---|---|---|---|---|
| COMPOSITION OF ADHESIVE LAYER (% BY WEIGHT) | RIVASTIGMINE | 15 | 18 | 25 | 36 | 5 | 10 |
| | ACRYLIC ADHESIVE A | 85 | 82 | 75 | 64 | — | — |
| | ACRYLIC ADHESIVE B | — | — | — | — | 95 | 90 |
| | STEARYL ALCOHOL | — | — | — | — | — | — |
| | LIGHT SILICIC ANHYDRIDE | — | — | — | — | — | — |
| THICKNESS OF ADHESIVE LAYER (μm) | | 50 | 100 | 72 | 50 | 250 | 150 |
| EVALUATION | STORAGE STABILITY (DRUG CONCENTRATION) | 100% | 100% | 100% | 100% | 99% | 99% |
| | STORAGE STABILITY (ANTI-COLD FLOW PROPERTY) | 100% | 100% | 100% | 99% | 100% | 100% |
| | PERMEABILITY TEST (mg/cm$^2$/24 hr) | 1.05 | 1.19 | 1.15 | 1.21 | 0.36 | 0.72 |
| | PATCH TEST AT 6 HOURS AFTER PASTING | GOOD | GOOD | GOOD | GOOD | GOOD | GOOD |
| | AT 24 HOURS AFTER PASTING | GOOD | GOOD | GOOD | GOOD | GOOD | GOOD |

| | | EXAMPLE 7 | EXAMPLE 8 | EXAMPLE 9 | EXAMPLE 10 | EXAMPLE 11 | EXAMPLE 12 |
|---|---|---|---|---|---|---|---|
| COMPOSITION OF ADHESIVE LAYER (% BY WEIGHT) | RIVASTIGMINE | 15 | 18 | 25 | 36 | 18 | 18 |
| | ACRYLIC ADHESIVE A | — | — | — | — | — | — |
| | ACRYLIC ADHESIVE B | 85 | 82 | 75 | 64 | 81 | 81.5 |
| | STEARYL ALCOHOL | — | — | — | — | 1 | — |
| | LIGHT SILICIC ANHYDRIDE | — | — | — | — | — | 0.5 |
| THICKNESS OF ADHESIVE LAYER (μm) | | 50 | 100 | 72 | 50 | 100 | 100 |
| EVALUATION | STORAGE STABILITY (DRUG CONCENTRATION) | 99% | 99% | 100% | 99% | 99% | 99% |
| | STORAGE STABILITY (ANTI-COLD FLOW PROPERTY) | 100% | 100% | 99% | 99% | 100% | 100% |
| | PERMEABILITY TEST (mg/cm$^2$/24 hr) | 0.83 | 1.00 | 1.05 | 1.34 | 1.34 | 1.21 |
| | PATCH TEST AT 6 HOURS AFTER PASTING | GOOD | GOOD | GOOD | GOOD | GOOD | GOOD |

TABLE 1-continued

| | | | | | | |
|---|---|---|---|---|---|---|
| AT 24 HOURS AFTER PASTING | GOOD | GOOD | GOOD | GOOD | GOOD | GOOD |

TABLE 2

| | | COMPARATIVE EXAMPLE 1 | COMPARATIVE EXAMPLE 2 | COMPARATIVE EXAMPLE 3 | COMPARATIVE EXAMPLE 4 |
|---|---|---|---|---|---|
| COMPOSITION OF ADHESIVE LAYER (% BY WEIGHT) | RIVASTIGMINE | 18 | 18 | 18 | 18 |
| | ACRYLIC ADHESIVE A | — | — | — | — |
| | ACRYLIC ADHESIVE B | — | — | — | — |
| | ACRYLIC ADHESIVE C | 81.9 | — | — | — |
| | POLYISOCYANATE | 0.1 | — | — | — |
| | HIGH MOLECULAR WEIGHT POLYISOBUTYLENE | — | 52 | — | — |
| | MEDIUM MOLECULAR WEIGHT POLYISOBUTYLENE | — | 30 | — | — |
| | STYRENE-ISOPRENE-STYRENE COPOLYMER | — | — | 32 | — |
| | HYDROGENATED PETROLEUM RESIN (ARKON) | — | — | 50 | — |
| | SILICONE ADHESIVE | — | — | — | 81 |
| | SILICONE OIL | — | — | — | 1 |
| | THICKNESS OF ADHESIVE LAYER (μm) | 100 | 100 | 100 | 100 |
| EVALUATION | STORAGE STABILITY (DRUG CONCENTRATION) | 95% | 95% | 98% | 100% |
| | STORAGE STABILITY (ANTI-COLD FLOW PROPERTY) | 100% | 97% | 11% | 66% |
| | PERMEABILITY TEST (mg/cm²/24 hr) | 0.56 | 0.73 | 2.00 | 1.80 |
| PATCH TEST | AT 6 HOURS AFTER PASTING | GOOD | BAD | BAD | BAD |
| | AT 24 HOURS AFTER PASTING | GOOD | VERY BAD | BAD | BAD |

INDUSTRIAL APPLICABILITY

The adhesive patch of the present invention has excellent storage stability and an increased skin permeability of rivastigmine to such an extent that the amount of percutaneous absorption required for treating Alzheimer's disease is obtained. Therefore, such an adhesive patch is suitably used as a transdermal preparation of rivastigmine.

The invention claimed is:

1. An adhesive patch comprising: a backing; and an adhesive layer containing rivastigmine and an alkyl (meth)acrylate-based copolymer without containing any acrylic monomer component having a carboxy group, the adhesive layer being laid on one side of and integrated with the backing,
    wherein the alkyl (meth)acrylate-based copolymer includes a copolymer containing a 2-ethylhexyl acrylate component, a 2-ethylhexyl methacrylate component and an alkyl (meth)acrylate component having an alkyl group with six or more carbon atoms except 2-ethylhexyl (meth)acrylate,
    wherein a total amount of the 2-ethylhexyl acrylate component and the 2-ethylhexyl methacrylate component is from 40 to 95% by weight of the copolymer, and an amount of the alkyl (meth)acrylate component having an alkyl group with six or more carbon atoms except 2-ethylhexyl (meth)acrylate is from 5 to 60% by weight of the copolymer.

2. The adhesive patch according to claim 1, wherein the alkyl (meth)acrylate component has an alkyl group with 6 to 16 carbon atoms except 2-ethylhexyl (meth)acrylate.

3. The adhesive patch according to claim 1, wherein the alkyl (meth)acrylate-based copolymer includes a 1-vinyl-2-pyrrolidone component.

4. The adhesive patch according to claim 1, wherein the alkyl (meth)acrylate-based copolymer includes a copolymer (B) containing a 1-vinyl-2-pyrrolidone component and an alkyl acrylate component having an alkyl group with 1 to 12 carbon atoms.

5. The adhesive patch according to claim 1, wherein rivastigmine is in a free base form.

6. The adhesive patch according to claim 1, wherein the adhesive layer does not contain an antioxidant and a rivastigmine volatilization inhibitor.

* * * * *